United States Patent [19]

Frazer et al.

[11] Patent Number: 6,013,262
[45] Date of Patent: *Jan. 11, 2000

[54] RECOMBINANT PAPILLOMA VIRUS L1

[75] Inventors: Ian Frazer, St. Lucia, Australia; Jian Zhou, Maywood, Ill.

[73] Assignee: The University of Queensland, Queensland, Australia

[ * ] Notice: This patent issued on a continued prosecution application filed under 37 CFR 1.53(d), and is subject to the twenty year patent term provisions of 35 U.S.C. 154(a)(2).

[21] Appl. No.: 08/737,336

[22] PCT Filed: May 17, 1995

[86] PCT No.: PCT/AU95/00292

§ 371 Date: Jan. 16, 1997

§ 102(e) Date: Jan. 16, 1997

[87] PCT Pub. No.: WO95/31476

PCT Pub. Date: Nov. 23, 1995

[30] Foreign Application Priority Data

May 17, 1994 [AU] Australia .............................. PM 5667

[51] Int. Cl.$^7$ ............................. A61K 39/12; C12Q 1/70; C12N 15/34

[52] U.S. Cl. ........................... 424/204.1; 435/5; 435/7.1; 435/69.1; 435/69.3; 435/252.3; 435/325.1; 435/320.1; 435/235.1; 435/253.33; 530/350; 530/403; 536/23.72

[58] Field of Search ............................... 435/69.1, 5, 7.1, 435/69.3, 252.3, 325.1, 320.1, 235.1, 253.33; 530/350, 403; 536/23.72; 424/204.1

[56] References Cited

U.S. PATENT DOCUMENTS 5,855,891  1/1999  Lowy et al. ......................... 424/192.1

FOREIGN PATENT DOCUMENTS

93/02184  2/1993  WIPO .

OTHER PUBLICATIONS

Rose et al. 1993, J. of Virology, vol. 67 (4), pp. 1936–1944.
Pohlner et al, 1993, Gene, vol. 130 (1), pp. 121–126.
H. M. Browne et al., "Analysis of the L1 Gene Product of Human Papillomavirus Type 16 by Expression in a Vaccinia Virus Recombinant", J. Gen. Virol., vol. 69, (1988), pp. 1263–1273.
D. S. Park et al., "Human Papillomavirus Type 16 E6, E7 and L1 and Type 18 E7 Proteins by Recombinant Baculoviruses", Journal of Virological Methods, vol. 45, (1993), pp. 303–318.
D. G. Strike et al., "Expression in Escherichia Coli of Seven DNA Fragments Comprising the Complete L1 and L2 Open Reading Frames of Human Papillomavirus Type 6b and Localization of the 'Common Antigen' Region", J. Gen. Virol., vol. 70, (1989), pp. 543–555.
J. Zhou et al., "Definition of Linear Antigenic Regions of the HPV16 L1 Capsid Protein Using Synthetic Virion–Like Particles", Virology, vol. 189, (1992), pp. 592–599.
J. Zhou et al., "The Induction of Cytotoxic T–Lymphocyte Precursor Cells by Recombinant Vaccinia Virus Expressing Human Papillomavirus Type 16 L1", Virology, vol. 181, (1991), pp. 203–210.
E. J. Androphy et al., "Identification of the HPV–16 E6 Protein from Transformed Mouse Cells and Human Cervical Carcinoma Cell Lines", The EMBO Journal, vol. 6, No. 4, (1987), pp. 989–992.
L. Banks et al., "Identification of Human Papillomavirus Type 18 E6 Polypeptide in Cells Derived from Human Cervical Carcinomas", J. Gen. Virol., vol. 68, (1987), pp. 1351–1359.
J. M. Firzlaff et al., "Detection of Human Papillomavirus Capsid Antigens in Various Squamous Epithelial Lesions Using Antibodies Directed Againse the L1 and L2 Open Reading Frames", Virology vol. 164, (1988), pp. 467–477.
T. Oltersdorf et al., "Identification of Human Papillmavirus Type 16 E7 Protein by Monoclonal Antibodies", J. Gen. Virol., vol. 68, (1987), pp. 2933–2938.
A. Schneider–Gaedicke et al., "Identification of the Human Papillomavirus Type 18 E6 and E6 Proteins in Nuclear Protein Fractions from Human Cervical Carcinoma Cells Grown in the Nude Mouse or in Vitro", Cancer Research, vol. 48, Jun. (1988), pp. 2969–2974.
K. Seedorf et al., "Identification of Early Proteins of the human Papilloma Viruses Type 16 (HPV 16) and Type 18 (HPV 18) in Cervical Carcinoma Cells", The EMBO Journal, vol. 6, No. 1, (1987), pp. 139–144.
D. Smotkin et al., "Transcription of Human Papillmavirus Type 16 Early Genes in a Cervical Cancer and a Cancer–Derived Cell Line and Identification of the E7 Protein", Proc. Natl. Acad. Sci. USA, vol. 83, Jul. (1986), pp. 4680–4684.
Stauffer, S. et al. "Expression of human papillomavirus type 18(HPV18) capsid proteins in E. coli and mammillian cells,".
Experimentia: 26$^{th}$ Annual Meeting of the Swiss Societies for Experimental Biology.
(USGEB/USSBE), vol. 50, p. A9, XP002101770 Abstract S04–05, Feb. 1994.
"pTrcHis A, B, & C," Invitrogen Corporation Catalogue, XP–0021000097, pp. 46, 47, 60, and 61 (1992).
S.A. Jenison et al., "Characterization of Human Antibody–Reactive Epitopes Encoded by Human Papillomavirus Types 16 and 18," J. Virol., vol. 65, No. 3, pp. 1208–1218 (Mar. 1991).
E. Schwartz et al., "DNA Sequence and genome organization of genital human papillomavirus type 6b," EMBO Journal, vol. 2, No. 12, pp. 2341–2348 (1983).

*Primary Examiner*—Mary E. Mosher
*Assistant Examiner*—Ali R. Salimi
*Attorney, Agent, or Firm*—Foley & Lardner

[57] ABSTRACT

This invention relates to a recombinant papilloma virus L1 protein which can elicit an immune response which recognises papilloma virus VLP including L1 protein and can form extracellularly a multimeric structure or VLP wherein the multimeric structure comprises a plurality of recombinant papilloma virus L1 proteins. This invention also includes the use of the recombinant papilloma virus L1 protein to detect the presence of papilloma virus and can form the basis of a vaccine for prophylactic and therapeutic use.

32 Claims, 4 Drawing Sheets

FIG. 1(a)

HEXAHIS leader

ATGCGGGGTTCTCATCATCATCATCATCATGGTATGGCTAGCATGACTGGTGGACAGCAA
MetArgGlySerHisHisHisHisHisHisGlyMetAlaSerMetThrGlyGlyGlnGln

ATGGGTCGGGATCTGTACGACGATGACGATAAGGAT
    MetGlyArgAspLeuTyrAspAspAspAspLysAsp   HPV6BL1

5820  ATGTGGCGGCCTAGCGACAGCACAGTATATGT
      TACACCGCCGGATCGCTGTCGTGTCATATACA       MetTrpArgProSerAspSerThrValTyrVal 5880
GCCTCCTCCTAACCCTGTATCCAAAGTTGTTGCCACGGATGCTTATGTTACTCGCACCAA
CGGAGGAGGATTGGGACATAGGTTTCAACAACGGTGCCTACGAATACAATGAGCGTGGTT ProProProAsnProValSerLysValValAlaThrAspAlaTyrValThrArgThrAsn 5940
CATATTTTATCATGCCAGCAGTTCTAGACTTCTTGCAGTGGGACATCCTTATTTTTCCAT
GTATAAAATAGTACGGTCGTCAAGATCTGAAGAACGTCACCCTGTAGGAATAAAAAGGTA IlePheTyrHisAlaSerSerSerArgLeuLeuAlaValGlyHisProTyrPheSerIle 6000
AAAACGGGCTAACAAAACTGTTGTGCCAAAGGTGTCAGGATATCAATACAGGGTATTTAA
TTTTGCCCGATTGTTTTGACAACACGGTTTCCACAGTCCTATAGTTATGTCCCATAAATT LysArgAlaAsnLysThrValValProLysValSerGlyTyrGlnTyrArgValPheLys 6060
GGTGGTGTTACCAGATCCTAACAAATTTGCATTGCCTGACTCGTCTCTTTTCGATCCCAC
CCACCACAATGGTCTAGGATTGTTTAAACGTAACGGACTGAGCAGAGAAAAGCTAGGGTG ValValLeuProAspProAsnLysPheAlaLeuProAspSerSerLeuPheAspProThr 6120
AACACAACGTTTAGTATGGGCATGCACAGGCCTAGAGGTGGGCAGGGGACAGCCATTAGG
TTGTGTTGCAAATCATACCCGTACGTGTCCGGATCTCCACCCGTCCCCTGTCGGTAATCC ThrGlnArgLeuValTrpAlaCysThrGlyLeuGluValGlyArgGlyGlnProLeuGly 6180
TGTGGGTGTAAGTGGACATCCTTTCCTAAATAAATATGATGATGTTGAAAATTCAGGGAG
ACACCCACATTCACCTGTAGGAAAGGATTTATTTATACTACTACAACTTTTAAGTCCCTC ValGlyValSerGlyHisProPheLeuAsnLysTyrAspAspValGluAsnSerGlySer

FIG. 1(b)

```
TGGTGGTAACCCTGGACAGGATAACAGGGTTAATGTAGGTATGGATTATAAACAAACACA
ACCACCATTGGGACCTGTCCTATTGTCCCAATTACATCCATACCTAATATTTGTTTGTGT

GlyGlyAsnProGlyGlnAspAsnArgValAsnValGlyMetAspTyrLysGlnThrGln

6300
ATTATGCATGGTTGGATGTGCCCCCCCTTTGGGCGAGCATTGGGGTAAAGGTAAACAGTG
TAATACGTACCAACCTACACGGGGGGGAAACCCGCTCGTAACCCCATTTCCATTTGTCAC

LeuCysMetValGlyCysAlaProProLeuGlyGluHisTrpGlyLysGlyLysGlnCys

6360
TACTAATACACCTGTACAGGCTGGTGACTGCCCGCCCTTAGAACTTATTACCAGTGTTAT
ATGATTATGTGGACATGTCCGACCACTGACGGGCGGGAATCTTGAATAATGGTCACAATA

ThrAsnThrProValGlnAlaGlyAspCysProProLeuGluLeuIleThrSerValIle

6420
ACAGGATGGCGATATGGTTGACACAGGCTTTGGTGCTATGAATTTTGCTGATTTGCAGAC
TGTCCTACCGCTATACCAACTGTGTCCGAAACCACGATACTTAAAACGACTAAACGTCTG

GlnAspGlyAspMetValAspThrGlyPheGlyAlaMetAsnPheAlaAspLeuGlnThr

6480
CAATAAATCAGATGTTCCTATTGACATATGTGGCACTACATGTAAATATCCAGATTATTT
GTTATTTAGTCTACAAGGATAACTGTATACACCGTGATGTACATTTATAGGTCTAATAAA

AsnLysSerAspValProIleAspIleCysGlyThrThrCysLysTyrProAspTyrLeu

6540
ACAAATGGCTGCAGACCCATATGGTGATAGATTATTTTTTTTTCTACGGAAGGAACAAAT
TGTTTACCGACGTCTGGGTATACCACTATCTAATAAAAAAAAGATGCCTTCCTTGTTTA

GlnMetAlaAlaAspProTyrGlyAspArgLeuPhePhePheLeuArgLysGluGlnMet

6600
GTTTGCCAGACATTTTTTTAACAGGGCTGGCGAGGTGGGGGAACCTGTGCCTGATACACT
CAAACGGTCTGTAAAAAAATTGTCCCGACCGCTCCACCCCCTTGGACACGGACTATGTGA

PheAlaArgHisPhePheAsnArgAlaGlyGluValGlyGluProValProAspThrLeu

6660
TATAATTAAGGGTAGTGGAAATCGCACGTCTGTAGGGAGTAGTATATATGTTAACACCCC
ATATTAATTCCCATCACCTTTAGCGTGCAGACATCCCTCATCATATATACAATTGTGGGG

IleIleLysGlySerGlyAsnArgThrSerValGlySerSerIleTyrValAsnThrPro

6720
GAGCGGCTCTTTGGTGTCCTCTGAGGCACAATTGTTTAATAAGCCATATTGGCTACAAAA
CTCGCCGAGAAACCACAGGAGACTCCGTGTTAACAAATTATTCGGTATAACCGATGTTTT

SerGlySerLeuValSerSerGluAlaGlnLeuPheAsnLysProTyrTrpLeuGlnLys
```

FIG. 1(c)

```
6780
AGCCCAGGGACATAACAATGGTATTTGTTGGGGTAATCAACTGTTTGTTACTGTGGTAGA
TCGGGTCCCTGTATTGTTACCATAAACAACCCCATTAGTTGACAAACAATGACACCATCT

AlaGlnGlyHisAsnAsnGlyIleCysTrpGlyAsnGlnLeuPheValThrValValAsp

6840
TACCACACGCAGTACCAACATGACATTATGTGCATCCGTAACTACATCTTCCACATACAC
ATGGTGTGCGTCATGGTTGTACTGTAATACACGTAGGCATTGATGTAGAAGGTGTATGTG

ThrThrArgSerThrAsnMetThrLeuCysAlaSerValThrThrSerSerThrTyrThr

6900
CAATTCTGATTATAAAGAGTACATGCGTCATGTGGAAGAGTATGATTTACAATTTATTTT
GTTAAGACTAATATTTCTCATGTACGCAGTACACCTTCTCATACTAAATGTTAAATAAAA

AsnSerAspTyrLysGluTyrMetArgHisValGluGluTyrAspLeuGlnPheIlePhe

6960
TCAATTATGTAGCATTACATTGTCTGCTGAAGTAATGGCCTATATTCACACAATGAATCC
AGTTAATACATCGTAATGTAACAGACGACTTCATTACCGGATATAAGTGTGTTACTTAGG

GlnLeuCysSerIleThrLeuSerAlaGluValMetAlaTyrIleHisThrMetAsnPro

7020
CTCTGTTTTGGAAGACTGGAACTTTGGGTTATCGCCTCCCCCAAATGGTACATTAGAAGA
GAGACAAAACCTTCTGACCTTGAAACCCAATAGCGGAGGGGGTTTACCATGTAATCTTCT

SerValLeuGluAspTrpAsnPheGlyLeuSerProProProAsnGlyThrLeuGluAsp

7080
TACCTATAGGTATGTGCAGTCACAGGCCATTACCTGTCAAAAGCCCACTCCTGAAAAGGA
ATGGATATCCATACACGTCAGTGTCCGGTAATGGACAGTTTTCGGGTGAGGACTTTTCCT

ThrTyrArgTyrValGlnSerGlnAlaIleThrCysGlnLysProThrProGluLysGlu

7140
AAAGCCAGATCCCTATAAGAACCTTAGTTTTTGGGAGGTTAATTTAAAAGAAAAGTTTTC
TTTCGGTCTAGGGATATTCTTGGAATCAAAAACCCTCCAATTAAATTTTCTTTTCAAAAG

LysProAspProTyrLysAsnLeuSerPheTrpGluValAsnLeuLysGluLysPheSer

7200
TAGTGAATTGGATCAGTATCCTTTGGGACGCAAGTTTTTGTTACAAAGTGGATATAGGGG
ATCACTTAACCTAGTCATAGGAAACCCTGCGTTCAAAAACAATGTTTCACCTATATCCCC

SerGluLeuAspGlnTyrProLeuGlyArgLysPheLeuLeuGlnSerGlyTyrArgGly

7260
ACGGTCCTCTATTCGTACAGGTGTTAAGCGCCCTGCTGTTTCCAAAGCCTCTGCTGCCCC
TGCCAGGAGATAAGCATGTCCACAATTCGCGGGACGACAAAGGTTTCGGAGACGACGGGG

ArgSerSerIleArgThrGlyValLysArgProAlaValSerLysAlaSerAlaAlaPro

TAAACGTAAGCGCGCCAAAACTAAAAGGTAA    7291
              ATTTGCATTCGCGCGGTTTTGATTTTCCATT

LysArgLysArgAlaLysThrLysArgTer
```

RECOMBINANT PAPILLOMA VIRUS L1

This is a rule 371 application based on the priority date of PCT/AU95/00292 filed May, 17, 1995.

FIELD OF THE INVENTION

THIS INVENTION relates to the L1 protein papilloma viruses. In particular, the invention relates to recombinant papilloma virus L1 protein and its use for detecting and treating papilloma virus infections.

BACKGROUND OF THE INVENTION

Papilloma viruses infect a range of hosts including man, cattle, sheep, dogs and cats. For a more complete listing, see "Papilloma Virus Infections in Animals" by J. P. Sundberg which is described in Papilloma Viruses and Human Diseases, edited by K. Syrjanen, L. Gissman and L. G. Koss, Springer Verlag, 1987.

Human papilloma viruses induce benign hyperproliferative lesions of the cutaneous and mucosal epithelia. Of the 70 different virus types which infect humans, more than 20 are associated with anogenital lesions (de Villiers, 1989, J. Virol. 63 4898–4903). Papilloma viruses have also been associated with various forms of cancers. Human papilloma virus types 16 and 18 have been associated with a number of cervical intra-epithelial neoplasias and carcinomas of the cervix (Lancaster et al., 1987, Cancer Metast. Rev. 6 6653–6664 and Pfister, 1987, Adv. Cancer Res. 48 113–147).

Papilloma viruses are small DNA viruses encoding up to eight early and two late genes. The late genes L1 and L2 code for structural proteins which assemble into a capsid within the cell (Galloway et al., 1989, Adv. Virus Res. 37 125–171). A single virus capsid is a T=7d icosahedron composed of 360 pentameric capsomers, each of which contains five molecules of the major capsid protein L1 (Baker et al., 1991, Biophys. J. 60 1445–1456 and Finch et al., 1965, J. Mol. Bio. 13 1–12). The minor capsid protein L2 is present at approximately one-tenth the abundance of L1 (Doorbar et al., 1987, J. Virol. 61 2793–2799).

Propagation of human papilloma viruses in vitro has not been achieved (Taichman et al., 1984, J. Invest. Dermatol. 83 25) and only small amounts of HPV proteins have been isolated from infected tissues (Androphy etal., 1987, Embo J. 6 1989; Banks et al., 1987, J. Gen. Virol. 68 1351; Firzlaff et al., 1988, Virology 164 467; Oltersdorf et al., 1987, J. Gen. Virol. 68 2933; Schneider-Gadicke et al., 1988, Cancer Res. 48 2969; Seedorf et al., Embo J. 6 139 and Smotkin et al., 1986, PNAS 83 4680). However, the gene coding for L1 protein has been cloned and expressed in a eukaryotic expression system using recombinant vaccinia virus (Browne etal., 1988, J. Gen. Virol. 69 1263–1273; Zhou et al., 1990, J. Gen. Virol. 71 2185–2190 and Zhou et al., 1991, Virology 185 251–257), in a baculovirus expression system (Park et al., 1993, J. Virol. Meth. 45 303–318) and in a bacterial expression system (Strike et al., 1989, J. Gen. Virol. 70 543–555).

As L1 protein is the major capsid protein, it has been used as the basis for the development of vaccines for protection against papilloma virus infection. Zhou et al. immunized mice with synthetic HPV16 virus-like particles (VLPs) using a vaccinia virus doubly recombinant for the L1 and L2 proteins of HPV16. The murine anti-VLP anti-sera recognised HPV16 capsids by ELISA and baculovirus recombinant HPV16L1 and L2 protein on immunoblot. The murine anti-VLP anti-sera, however, failed to recognise two peptides that were recognised by anti-HPV16L1 monoclonal antibodies raised against a recombinant L1 fusion protein (Zhou et al., 1992, Virology 189 592–599). These researchers concluded that the immunoreactive epitopes of HPV16 defined using virus-like particles differ significantly from those defined using recombinant HPV16L1 fusion proteins.

To overcome problems of presentation, vaccines were developed using virus-like particles. VLPs were formed intracellularly from recombinant L1 or L1 and L2 proteins encoded by recombinant vaccinia virus (Zhou et al., 1991, Virology 185 251–257; Zhou et al., 1991, Virology 181 203–210 and International Patent Specification WO93/02184). These vaccines using synthetic virus-like particles have a number of disadvantages. Firstly, the recombinant L1 or L1 and L2 genes are expressed from a vaccinia virus vector which may not be suitable for the production of a vaccine. Secondly, the virus-like particles are produced intracellularly which is a rate limiting step. Thirdly, the virus-like particles may incorporate cellular DNA because they are produced intracellularly and virus-like particles incorporating DNA are not suitable for use in vaccines. Fourthly, virus-like particles may only be partially purified because of the need to retain their integrity and hence correct epitope presentation. Consequently, other proteins or matter associated with the virus-like particles may contaminate a vaccine preparation. Fifthly, the process of producing a vaccine in commercial amounts with virus-like particles from recombinant vaccinia viruses is comparatively expensive.

Similar disadvantages apply to the use of the virus-line particles produced from recombinant vaccinia viruses for the detection of antibodies in the sera of patients.

SUMMARY OF THE INVENTION

The present invention results from the surprising discovery that a recombinant papilloma virus L1 protein can form multimeric structures extracellularly and elicit an immune response that recognises native papilloma virus capsids.

Thus it is an object of the present invention to provide a recombinant papilloma virus L1 protein that can form an immunogenic multimeric structure.

In one aspect, the invention is a recombinant papilloma virus L1 protein which has an N terminal amino acid sequence including $(His)_6$. $(His)_6$ represents six linked histidine residues.

The recombinant papilloma virus L1 protein may have an N terminal amino acid sequence which includes:

MetArgGlySerHisHisHisHisHisHisGlyMetAlaSerMetThrGlyGlyGlnGlnMetGlyArgAspLeuTyrAspAspAspAspLysAsp (SEQ ID NO:1).

Figure 1A:
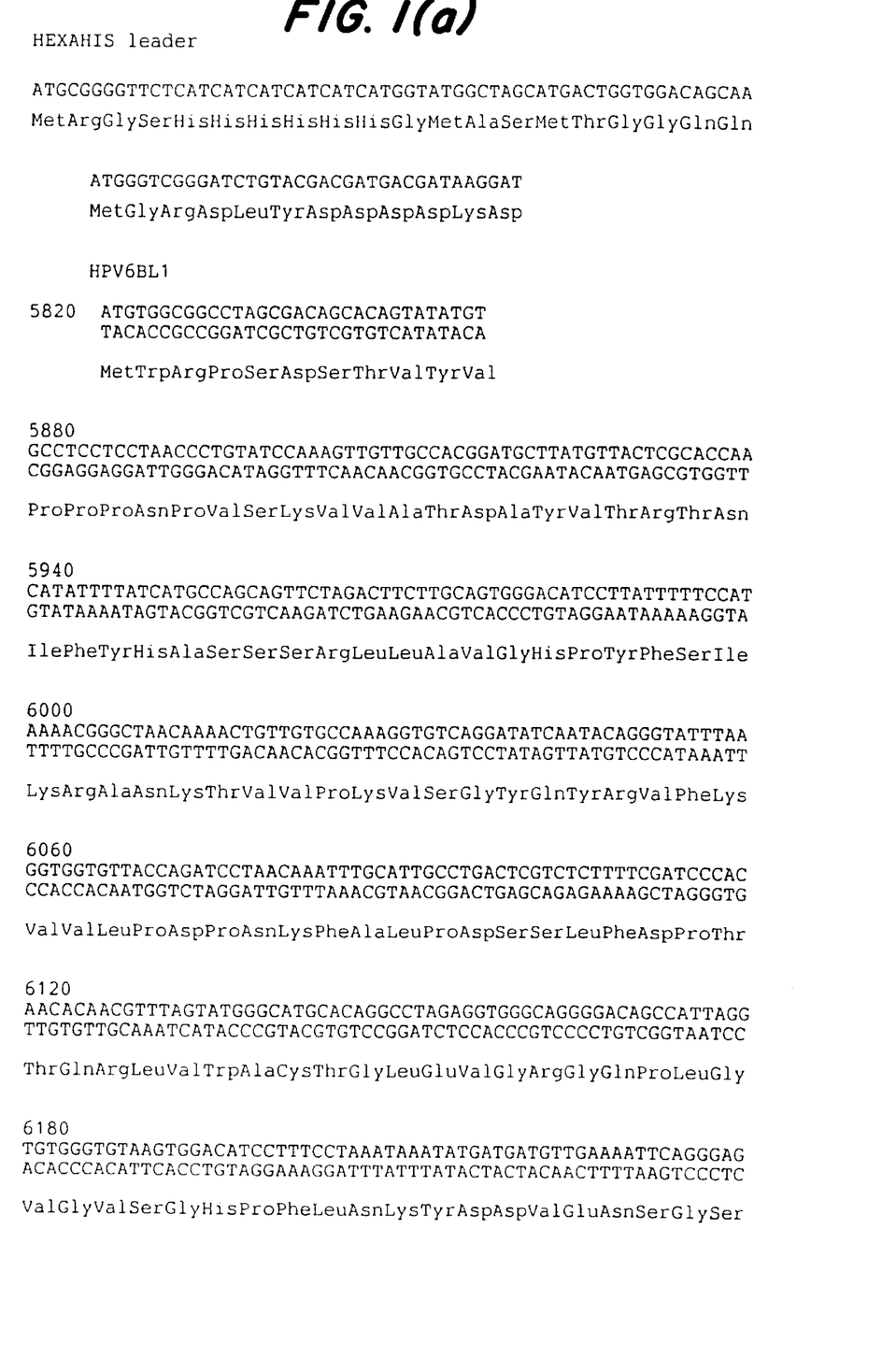

The recombinant papilloma virus L1 protein may be derived from any papilloma virus type. The recombinant papilloma virus L1 protein may be an entire or partial amino acid sequence of a papilloma virus L1 protein. The recombinant papilloma virus L1 protein may be an amino acid sequence coding for one or more epitopes that elicit an immune response which recognises papilloma virus VLP. By way of example, the recombinant papilloma virus L1 protein is derived from HPV 6b and the recombinant papilloma virus L1 protein is shown in FIGS. 1(a)–1(c).

The immune response elicited by the recombinant papilloma virus L1 protein may be an antibody response, or an antibody response together with a cell mediated response. The elicited response may recognise recombinant and/or native papilloma virus VLP L1 protein. The antibody response is where antibodies are raised against the recombinant papilloma virus L1 protein and these antibodies recognise papilloma virus VLP L1 protein. The cell mediated and humoral response may include T cells, large granular lymphocytes, mononuclear phagocytes, neutrophils, eosinophils, basophils, mast cells, various tissue cells, platelets, complement, inflammatory mediators and cytokines including interferons, interleukins, colony stimulating factor, tumor necrosis factor and transforming growth factor B. The cell mediated and humoral response may result from being primed and challenged with recombinant papilloma virus L1 protein. An example of a cell mediated and humoral response is delayed type hypersensitivity.

In a second aspect, the invention is a multimeric structure comprising a plurality of recombinant papilloma virus L1 proteins; each of said recombinant papilloma virus L1 proteins having an N terminal amino acid sequence including (His)$_6$ One or more of the recombinant papilloma virus L1 proteins may have an N terminal amino acid sequence as described above.

The multimeric structure may be any size but preferably it is a pentameric structure. A multimeric structure may be a VLP. The term VLP includes papilloma virus virions and recombinant VLP. The multimeric structures are preferably formed after the recombinant papilloma virus L1 protein has been substantially purified. The multimeric structures may self-assemble extracellularly in suitable buffers. Further, the multimeric structure is able to induce an immune response that recognises papilloma virus VLP.

A third aspect of the invention is a recombinant DNA molecule which encodes a recombinant papilloma virus L1 protein according to the first aspect of the invention. The recombinant DNA molecule may encode a part of said recombinant papilloma virus L1 protein that includes epitopes that elicit an immune response which recognises papilloma virus VLP. Alternatively, the recombinant DNA molecule may be a synonymous DNA sequence that codes for said recombinant papilloma virus L1 protein or said part of said recombinant papilloma virus L1 protein. The recombinant DNA molecule may encode a sequence that can hybridise under standard conditions to a sequence encoding said recombinant papilloma virus L1 protein or said part of said recombinant papilloma virus L1 protein. The recombinant DNA molecule which encodes the recombinant papilloma virus L1 protein may have a 5' nucleotide sequence which includes six repeats of the trinucleotide sequence CAT. The recombinant DNA molecule which encodes the recombinant papilloma virus L1 protein may preferably have a 5' nucleotide sequence which includes:

ATGCGGGGTTCTCATCATCATCATCAT-CATGGTATGGCTAGCATGACTGGTGGA-CAGCAAATGGGTCGGGATCTGTACGAC-GATGACGATAAGGAT (SEQ ID NO:2).

A suitable recombinant DNA molecule is shown in FIGS. 1(a)–1(c).

A fourth aspect of the invention is a method for preparation of a multimeric structure comprising a plurality of recombinant papilloma virus L1 protein, said multimeric structure is able to induce an immune response that recognises papilloma virus VLP including the steps of:

(I) expressing a recombinant DNA molecule which encodes a recombinant papilloma virus L1 protein from a bacterium;

(II) substantially purifying the recombinant papilloma virus L1 protein; and (III) forming said multimeric structure extracellularly.

The method may use multimeric structures comprising recombinant papilloma virus L1 proteins which has an N terminal amino acid sequence that includes (His)$_6$. The N terminal amino acid sequence may include:

MetArgGlySerHisHisHisHisHisH-isGlyMetAlaSerMetThrGlyG-lyGlnGlnMetGlyArgAspLeu-TyrAspAspAspAspLysAsp (SEQ ID NO:1).

The recombinant DNA molecule may be constructed from a suitable source of papilloma virus DNA such as a human papilloma virus or a bovine papilloma virus using standard cloning and/or PCR techniques. The recombinant DNA molecule may also include an expression vector. The expression vector may be a plasmid, cosmid, phagemid or a virus. A suitable expression vector encodes (in the following order) an ATG site, (His)$_6$ peptide, and then a cloning site wherein papilloma virus L1 protein DNA sequence may be inserted in the correct reading frame so that a fusion protein of (His)$_6$-L1 protein results from translation. A preferable expression vector is any one of plasmids pTrcHisA, pTrcHisB and pTrcHisC. A suitable host is a *E. coli* strain.

The preferred expression system is a bacterial expression system with *E coli* and plasmid pTrcHisB. Introduction of the recombinant DNA molecule into a suitable host may be achieved by any suitable method including transfection and transformation. A preferable recombinant DNA molecule is the complete DNA sequence of HPV6b L1 protein inserted into pTrcHisB in a correct reading frame orientation to form pTrc6bL1. The recombinant DNA molecule pTrc6bL1 is preferably transformed into *E. coli* strain DH5.

Following expression, the expression system may be disrupted. Where the expression system is a cell system, the cell may be lysed with suitable techniques and agents such as sonication in a buffer containing guanidinium hydrochloride. The recombinant papilloma virus L1 protein may be partially or completely purified. Purification may be achieved by using any one or more suitable chromatographic procedures. The recombinant papilloma virus L1 protein may be purified using a step of affinity chromatography with a nickel column. Additional purification steps may include preparative gel electrophoresis.

In a fifth aspect, the invention provides a method for detecting the presence of papilloma virus.

The method may detect the presence of papilloma virus L1 protein in a sample using antibody raised against said papilloma virus L1 protein. The method may employ ELISA, RIA or other immunoassay techniques. The method may include the steps of:

(1) coating the wells of a microtitre plate with a sample which putatively contains papilloma virus L1 protein;

(2) adding antisera raised against the recombinant papilloma virus L1 protein to form a papilloma virus L1 protein-antibody complex; and (3) detecting the presence of the papilloma virus L1 protein-antibody complex with a detection agent.

With respect to step (1), the wells of the microtitre plate may be initially coated with antisera raised against the recombinant papilloma virus L1 protein prior to the addition of the sample. The detection agent may be an antibody or other suitable ligand conjugated with a suitable label. A suitable label may include any suitable enzyme label such as horseradish peroxidase, a radioactive isotope or a fluorometric molecule.

In a sixth aspect, the invention provides a method for detecting the presence of antibodies specific for papilloma virus L1 proteins in a sample using said recombinant papilloma virus L1 protein.

The method may employ ELISA, RIA or other immunoassay techniques. The method may include the steps of:

(i) coating the wells of a microtitre plate with the recombinant papilloma virus L1 protein;

(ii) adding the sample which putatively contains antibody specific for papilloma virus L1 protein to form a recombinant papilloma virus L1 protein-antibody complex; and (iii) detecting the presence of recombinant papilloma virus L1-antibody complex with a detection agent.

In a seventh aspect, the invention provides a kit for detecting the presence of papilloma virus L1 protein in a sample and includes antibody raised against said recombinant papilloma virus L1 protein.

In an eighth aspect, the invention provides for a kit for detecting the presence of antibody specific for papilloma virus L1 protein in a sample and includes said recombinant papilloma virus L1 protein.

In a ninth aspect, the invention provides for a prophylactic or therapeutic vaccine including said recombinant papilloma virus L1 protein. The vaccine may include a suitable adjuvant such as ISCOMS, alum, Freunds Incomplete adjuvant, Freunds Complete adjuvant, Quil A, other saponins, Aluminium hydroxide algammulin, and pertussigen. Alternatively, the vaccine may not include adjuvant where the recombinant papilloma virus L1 protein is immunogenic without adjuvant.

BRIEF DESCRIPTION OF THE DRAWINGS

FIGS. 1(a)–1(c) illustrate the DNA nucleotide sequence and amino acid sequence of HPV6bL1HEXAHIS protein (SEQ ID NOS:5 and 6)

Reference may now be made to various preferred embodiments of the invention. In these preferred embodiments, it should be noted that the references to specific papilloma viruses, vaccines and constructs of recombinant DNA molecules are given by way of example only.

EXPERIMENTAL

EXAMPLE 1

Production of HPV6b L1 HEXAHIS protein
Construction of pTRC6bL1

The L1 open reading frame of HPV6b was cloned from a clinical isolate by polymerase chain reaction using as primers:

G C
GGATCCAGATGTGGCGGCCTAGCGACAGCACA GTATATG and

CGCCCGGGTTACCTTTTAGTTTTGGCCTCGCTTA CGTTTTAGG (SEQ ID NOS:3 and 4).

The resulting 1.5 kb PCR product was cleaved with BamH1 and Sma1 and cloned into a BamH1/klenow blunted Eco R1 site created within the plasmid pTRCHIS B (Invitrogen). The resultant L1 recombinant plasmid was pTRC6bL1 and encodes a protein sequence:

Met.Arg.Gly.Ser.His.His.His.His.His.His.Gly.Met.Ala.Ser.Met.Thr.Gly.Gly. Gln.Gln.Met.Gly.Arg.Asp.Leu.Tyr.Asp.Asp.Asp.Lys.Asp. (HPV6b L1 aas1-520) (SEQ ID NO:1).

Growth of Bacteria encoding the HPV6b L1 HEXAHIS Protein 10 mls of 2YT broth (16 mg tyrptone, 10 mg yeast. 5 mg NaCl) containing Ampicillin (final concentration 100 µg/ml) was inoculated with 10 µl of one loopful of bacteria (E. coli DH5) from glycerol stock. The culture was incubated at 37° C. with aeration at 120 rpm for six hours.

200 mls of 2YT broth containing Ampicillin (final concentration 100 µg/ml) was inoculated with the six hour-10 ml culture. The culture was incubated at 37° C. with aeration at 120 rpm overnight.

800 mls of 2YT broth containing Ampicillin (final concentration 100 µg/ml) was inoculated with the 200 ml-overnight culture. The culture was incubated at 37° C. with aeration at 120 rpm until the absorbance reached between 0.6–0.8 O.D. units at 600 nm (usually 2–3 hours). The HPV6b L1 HEXAHIS protein was induced by addition of 0.5 mM IPTG for 4–6 hours.

The bacteria were pelleted by centrifugation (Beckman JA14 rotor centrifuged at 5000 rpm for 10 minutes at 20° C.). The pellet was washed in 50 ml of phosphate buffered saline by resuspending the bacterial pellet in a 50 ml centrifuged tube. The washed bacteria were repelleted by centrifugation (Beckman TJ-6 at 3000 rpm for 10 minutes at 20° C.). The supernatant was discarded. The pellet was stored at −20° C. or −70° C. until needed.

Purification of HPV6b L1 HEXAHIS Protein

The bacteria were resuspended and lysed in 50 ml of Guanidinium lysis buffer (6M Guanidinium hydrochloride and 5.8 ml/liter of solution A [177 mM $NaH_2PO_4$ and 5M NaCl] pH 7.8 using HCl). The suspension was sonicated at 30% output for two minutes. The cell debris was peileted by centrifugation (Beckman JA21 rotor at 10000 rpm for 30 minutes at 4° C.). The supernatant which contains the HPV6b L1 HEXAHIS protein was retained.

The HPV6b L1 HEXAHIS protein was substantially purified by essentially a two step purification procedure.

The supernatant containing the HPV6b L1 HEXAHIS protein was loaded onto a nickel column (2.6 cm×6 cm) using a BIORAD ECONO system at 4° C. Before loading the supernatant, the column was washed thoroughly with NA buffer at 1 ml/minute. NA buffer comprises 6M urea, 5.8 mls/liter solution A [177 mM $NaH_2PO_4$ and 5M NaCl], 94 mls/liter solution B [200 mM $Na_2HPO_4$ and 5M NaCl] at pH 7.8 using HCl before urea was added. The supernatant was loaded onto the Nickel column at one mi/minute. 10 ml fractions were collected in case the column was overloaded and any unbound protein was washed through the column. After the supernatant was loaded, the column was washed with NB buffer at a flow rate of one ml/minute. NB buffer comprises 6M urea and 100 mls/liter of solution A [177M $NaH_2PO_4$ and 5M NaCl] at pH 4.0 using HCl before urea is added. The column was washed with NB buffer according to the procedure in Table 1 where lowering of the pH gradient removed contaminating proteins. 10 ml fractions of the eluent were collected.

The fractions containing HPV6b L1 HEXAHIS protein were determined by either dot blot, direct ELISA or SDS PAGE. After the fractions were identified, the washing of the column continued with 100% NB buffer until the pH levelled off. The column was then washed with NA buffer. (The column was stored in 20% ethanol.)

The fractions containing HPV6b L1 HEXAHIS protein were pooled and dialysed against five liters of $dH_2O$ or 10 mM Tris HCl pH 7.5 for overnight at 4° C. (or two hours at room temperature). The protein was then precipitated with acetone in a 8:2 acetone to sample ratio, for two hours at −70° C. or overnight at −20° C. The protein-acetone solution was centrifuged (Beckman TJ-6 at 3000 rpm and at 4° C. for 20 minutes). The supernatant was discarded. The pellet was dried under a flow of nitrogen gas for five minutes to remove any remaining acetone.

The pellet was resuspended in 1 ml of $ddH_2O$ and 4–5 mls of 4× loading buffer [1.0 ml of 0.5M Tris pH 6.8, 0.8 ml of glycerol, 1.6 ml of 10% SDS w/v, 0.1 g of DTT 1% w/v, 0.2 ml of 0.1% w/v bromphenol blue and 4.4 ml of $dH_2O$]. The resuspended pellet was heated at 65–70° C. for 15 minutes to ensure all the protein was dissolved.

The resuspension was loaded onto a BIORAD Prep Cell comprising a 10% separating gel (4.5 cm high by 4 cm diameter) with a 4% stacking gel (4 cm high by 4 cm diameter). The Prep Cell was ran at 12 W constant power.

When the dye front of the gel reached 2 cm from the bottom, 10 ml fractions at a 1 ml/minute elution rate were collected. Fractions were tested for HPV6b L1 HEXAHIS protein by either dot blot, direct ELISA or SDS PAGE (with the Phast system). Positive fractions were tested on SDS PAGE and those found to have a single HPV 6bL1HEXAHIS protein band were pooled. The pooled fractions were dialysed against 5 liters of ddH$_2$O to remove glycine. Dialysis occurred overnight at a temperature of 4° C. and using two changes of ddH$_2$O.

The dialysed HPV6b L1 HEXAHIS protein was precipitated with acetone to remove SDS. A 8:2 acetone to sample ratio was used either for two hours at −70° C. or overnight at −20° C. The protein-acetone solution was centrifuged (Beckman TJ-6 at 3000 rpm and at 4° C. for 20 minutes). The supernatant was discarded and the pellet was dried under a flow of nitrogen gas for five minutes to remove any remaining acetone.

Figure 2:
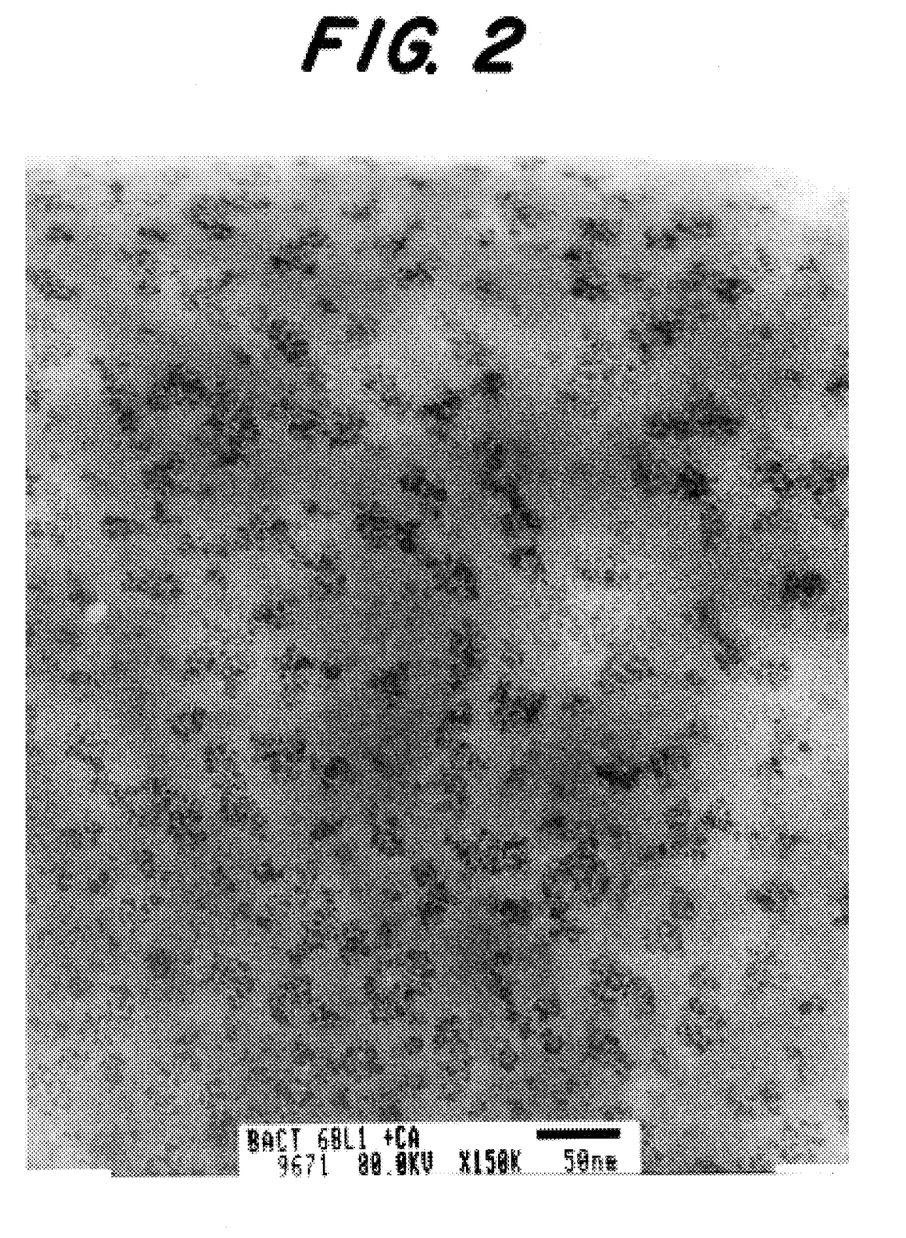
FIG. 2 is an electron micrograph of pentameric structures of HPV6bL1 HEXAHIS protein aggregates.

The protein was then able to be resuspended in a buffer of choice and its concentration determined. This protein was subsequently demonstrated to form capsomers by purifying the HPV6b L1 HEXAHIS protein as described, gradual removal of urea by dialysis against 10 mM Tris HCl pH 7.5, and examination of the resultant immunoprecipitate by scanning electron microscopy. FIG. 2 shows the typical pentameric structures of HPV6b L1 HEXAHIS protein aggregates.

EXAMPLE 2

Demonstration of antibody production against HPV6b L1 HEXAHIS protein

To produce antibody against HPV6b L1 HEXAHIS protein, mice (strain C57BI/6) were injected subcutaneously twice at a four week interval with 50 μg protein/mouse following the experimental protocol in Table 2. Two weeks after the second injection the mice were bled. Serum was obtained from the extracted blood using standard procedures.

The serum was tested for the production of antibodies to HPV6b L1 HEXAHIS protein using three different antigens.

The serum was tested against a human papilloma virus HPV6B capsid preparation. The serum was diluted at 1 in 200 and tested against a HPV6B capsid preparation in RIPA buffer (20 mM Tris-HCl pH 7.6; 2 mM EDTA; 50 mM NaCl; 1% deoxycholate; 1% Triton X-100; 0.25% SDS; 1% aprotinin, and 1 mM PMSF). The antibody-antigen precipitates were run on 10% SDS PAGE separating the individual components of the immune complex. The presence of HPV6b L1 protein was detected with rabbit anti-HPV6b L1 antibody. The presence of HPV6b L1 protein indicates anti-HPV6b L1 antibody was produced in the mouse against 6bL1HEXAHIS protein. Groups A, B, C, D,E and F gave positive results.

Serum was also tested by western blot analysis with HPV6b L1 produced from baculovirus. A positive result indicates anti-HPV6b L1 antibody was produced in the mouse against HPV6b L1 HEXAHIS protein. Groups A, B, C, D, E and F gave positive results with the best result demonstrated when aluminium hydroxide was used as adjuvant. The control groups A, B, C, D and E gave negative results.

The serum was tested by dot blot and ELISA using standard techniques against bovine papilloma virus L1 protein. The best result was achieved with serum from group D mice (i.e. when aluminium was used as an adjuvant) with a OD reading of 0.96. This was followed by serum from group C (i.e. with Freund's complete adjuvant) with OD reading of 0.70, serum from group E (ie. with algammulin) with OD reading 0.34, then serum from group B (i.e. boiled in 1% SDS and cooled) with OD reading 0.24 and serum from group A (no adjuvant) with OD reading 0.34. All control groups had an OD reading of 0.05.

The testing of the serum against three different antigens showed that the HPV6b L1 HEXAHIS protein was immunogenic and produced anti-HPV6b L1 antibodies when used as an antigen with or without adjuvant.

EXAMPLE 3

Demonstration of delayed type hypersensitivity (and confirm antibody production) in mice by HPV6b L1 HEXAHIS protein Delayed type hypersensitivity involves cell mediated immune reactions as well as some humoral immune reactions. Mice (strain BALB/c) were treated (intraperitoneal injection) with HPV6b L1 HEXAHIS protein under a variety of conditions outlined in Table 3. On day 11 the ear was challenged by intradermal injection) with HPV6b L1 HEXAHIS protein or another HEXAHIS protein. The thickness of the ear was measured on day 13 and day 14. Mice that gave a positive response on day 14 were killed and the histology of the ear was examined.

It was demonstrated in this example that HPV6b L1 HEXAHIS protein without adjuvant induced good delayed type hypersensitivity with initial doses of 50 μg/mouse but not at 5 μg/mouse. However, mice needed to be pertussigen treated to induce a delayed type hypersensitivity response.

With respect to the three examples, it has been shown that HPV6b L1 protein expressed and isolated in the method of Example 1 formed capsomeric aggregates, and the HPV6b L1 protein capsomeric aggregates without further adjuvant were immunogenic producing an antibody response and a cell mediated response. Therefore, HPV6b L1 HEXAHIS protein would serve as a suitable basis for a vaccine designed to prevent human papilloma virus infection by induction of neutralising antibodies or to treat existing lesions through the induction of L1 protein specific cell mediated immunity. Examples 1 to 3 have used HPV6b L1 protein as an example to demonstrate the immunogenicity of the preparation and, as an example, the invention is not restricted to this example and any papilloma virus L1 protein can be used.

EXAMPLE 4

Demonstration that antibodies raised to HPV6b L1 HEXAHIS protein recognise HPV6b L1 virus-like particles (VLPS)

Wells of plates were coated at 0.2 μg protein/well with either HPV6b L1 HEXAHIS produced from E. coli, HPV6 VLP-L1 produced from baculovirus, and baculovirus and E. coli preparations (cell fermentation supernatants) as controls, in PBS at pH 7.2 and left to incubate overnight at room temperature. One wash was conducted with PBS at pH 7.2. Non-specific binding was blocked by incubating the plates with 1% (w/v) casein for 1 hour at room temperature.

Rabbit HPV6b L1 HEXAHIS antisera was added to each of the wells coated with HPV6b L1 HEXAHIS, HPV VLP-1, baculovirus prepared controls or E. coli prepared controls (prepared in duplicate), and was serially diluted ½ down the plates. Sera raised against influenza virus A/PR-8 was used as a negative control. Sera raised against HPV VLP-L1 was used as positive control on HPV VLP-L1 plates. Plates were incubated for 1 hour, at room temperature, and were then washed three times with PBS containing 0.05% (v/v) Tween 20 at pH 7.2. Goat-rabbit IgG-HRP conjugate was added to each well and plates were incubated and washed as before. Specific binding of antisera to antigen was detected using TMB. The reaction was stopped after 5 minutes using 0.5M HCl.

Results

The results of the experiment are shown in Table 4. Both HPV6b L1 HEXAHIS protein and HPV6 VLP-L1 complexed with antibody raised against HPV6b L1 HEXAHIS protein indicating that HPV6b HEXAHIS L1 correctly presents in vivo one or more epitopes presented by HPV VLP-L1. The sera raised against HPV6 L1 protein was also negative in the baculovirus or *E. coli* wells demonstrating the specificity of the reaction. This provides support for the use of HPVL1 HEXAHIS as a vaccine immunogen suitable for inducing antibody which can interact with and potentially neutralise virus. Further, this example provides support for an immunoassay for the detection of papilloma virus L1 protein demonstrated by the coating of various proteins in wells and the use of antibody raised against recombinant HPV6 L1 HEXAHIS protein. Wells containing either HPV6b derived antigen gave a positive result. This example also provides support for an immunoassay for the detection of antibody specific for papilloma virus L1 protein demonstrated by the coating of the wells with recombinant HPV6b L1 HEXAHIS protein and the use of sera raised against influenza virus A/PR-8 and sera raised against HPV6 L1 HEXAHIS protein. In this case, wells containing sera raised against HPV6 L1 HEXAHIS protein gave a positive result whilst that raised againt influenza virus was negative.

EXAMPLE 5

ELISA capture assay demonstrating the formation of multimeric structure-antibody complex Western blot and ELISA experiments were conducted as previously described or following standard procedures. An ELISA capture assay was conducted by the following method:

(1) a monoclonal antibody (moAb 8) specific for VLPs was used to coat the wells of a microtitre plate;

(2) HPV VLP L1 protein was added and incubated under suitable conditions and washed with PBS containing 0.1% Tween 20 at pH 7.4;

(3) antibodies raised against various immunogens (shown in column 2 of Table 5) in various animals (shown in column 1 of Table 5) was added; and (4) suitable detection agents (in the case of rabbit antisera, goat-anti-rabbit peroxidase conjugate was used) were added to detect multimeric structure/VLP-antibody complex.

Results

The amount of captured recombinant papilloma virus HEXAHIS per well is given in Table 5. These experiments demonstrate that the antisera raised against recombinant papilloma virus L1 HEXAHIS proteins elicit an immune response which recognises papilloma virus VLP including L1 protein.

The ability of a papilloma virus L1 protein to elicit an immune response which recognises papilloma virus VLP including L1 protein requires correct presentation of appropriate epitopes. Recombinant papilloma virus L1 proteins that do not form VLP do not induce an immune response which recognises papilloma virus VLPs including L1 protein. Recombinant GST papilloma virus L1 protein, recombinant MS2 papilloma virus L1 protein and denatured papilloma virus L1 protein do not elicit an immune response which recognises papilloma virus VLP including L1 protein. All VLPs to date have been produced intracellularly with the expression of papilloma virus L1 or L1 and L2 genes. The recombinant papilloma virus L1 protein of the present invention correctly presents one or more epitopes to elicit an immune response which recognises papilloma virus VLP including L1 protein. The recombinant papilloma virus L1 protein of the present invention can form the multimeric structures or VLPs extracellularly. It is believed that the multimeric structures of VLPs formed from the recombinant papilloma virus L1 protein correctly presents one or more epitopes to elicit an immune response which recognises papilloma virus VLPs including L1 protein. Therefore, the invention provides a recombinant papilloma virus L1 protein which can form extracellularly a multimeric structure or VLP which can elicit an immune response which recognises papilloma virus VLP including L1 protein wherein said multimeric structure comprises a plurality of recombinant papilloma virus L1 proteins.

The fact that the multimeric structures or VLPs can be formed extracellularly overcomes a number of problems associated with intracellular VLP formation. These problems include low VLP levels, the possibility of incorporating DNA in the VLP and the possible loss of integrity of the VLP with purification.

TABLE 1

Procedure for washing the Nickel column with NB buffer

| Time (Minutes) | % NB Buffer |
| --- | --- |
| 0 | 0 |
| 30 | 0 |
| 300 | 100 |
| 310 | 100 |
| 320 | 100 |
| 330 | 100 |

TABLE 2

Experimental protocol for injecting mice with 6b L1 HEXAHIS protein to produce antibodies

| Mice Group[a] | Addition of 6b L1 HEXAHIS protein[b] | Other conditions |
| --- | --- | --- |
| A | + | No adjuvant |
| $A_1$ | − | No adjuvant |
| B | + | boiled in 1% SDS and cooled |
| $B_1$ | − | boiled in 1% SDS and cooled |
| C | + | with Freund's complete adjuvant |
| $C_1$ | − | with Freund's complete adjuvant |
| D | + | absorbed to Aluminium hydroxide |
| $D_1$ | − | absorbed to Aluminium hydroxide |
| E | + | with Algammulin |
| $E_1$ | − | with Algammulin |
| F | + | with L2 (50 μg) and no adjuvant |

TABLE 3

Experimental protocol for producing delayed type hypersensitivity to 6b L1 HEXAHIS protein in mice

| Mice Group[a] | Antigen[a] | Adjuvant[c] | Antigen dose | Challenge[b,d] | Pertussigen | Antigen dose | Mean Ear *Swelling Day 14[f] |
|---|---|---|---|---|---|---|---|
| 1 | L1 | PBS | 50 μg | L1 | + | 4 | 4.5 |
| 2 | L1 | PBS | 50 μg | L1 | + | 13.8 | 8 |
| 3 | L1 | PBS | 50 μg | L1 | − | 3.8 | 1.5 |
| 4 | L1 | PBS | 50 μg | L1 | − | 2.4 | 3.8 |
| 5 | L1 | PBS | 50 μg | IRR | + | | |
| 6 | Saline | PBS | | L1 | + | 4.7 | 1.3 |
| 7 | Saline | PBS | | L1 | − | 2.3 | 1 |
| 8 | L1 | CFA (0.1 ml) | 50 μg | L1 | + | 19.3 | 16.8 |
| 9 | Saline | CFA (0.1 ml) | | L1 | + | 4.8 | 2 |
| 10 | L1 | Quil A (pg) | 50 μg | L1 | + | 15.7 | 8.7 |
| 11 | L1 | Quil A (pg) | 50 μg | L1 | − | 7.2 | 0.2 |
| 12 | L1 | Quil A (pg) | 50 μg | IRR | + | | |
| 13 | Saline | Quil A (pg) | 50 μg | L1 | + | | |

TABLE 4

Results of ELISA using rabbit HPV6b L1 HEXAHIS antisera

| ANTIGEN | ELISA USING RABBIT HPV6b L1 HEXAHIS ANTISERA |
|---|---|
| HPV6 VLP-L1 | >4.0 exceeds limits @ 1:4000 |
| HPV6b L1 HEXAHIS | 2.12 ± 0.1 @ 1:4000 |
| baculovirus control preparation | 0.63 ± 0.01 @ 1:4000 |
| E. coli control preparation | 0.12 ± 0.00 @ 1:4000 |

TABLE 3
[a] Groups consist of 4 to 6 Balb/C mice (68–102)
[b] L1 denotes 6b L1 HEXAHIS protein and IRR denotes irrelevant HEXAHIS protein
[c] PBS is phosphate buffered saline and CFA is complete Freund's adjuvant
[d] 6b L1 HEXAHIS protein was administered at 10 μg in a maximum volume of 2 μl
[e] 30 μg of pertussigen was added
[f] Ear measurements (μm×10)
TABLE 5
ND: technically cannot be determined
FIGS. 1(a)–1(c)

TABLE 5

Results of experiments conducted in Example 5

| ANIMAL NO. | IMMUNOGEN | ADJUVANT | Western Blot | ELISA (VLPs) | Capture ELISA | L1 as VLP | L1 as HEXAHIS |
|---|---|---|---|---|---|---|---|
| Rabbit 31 | HEXAHIS L1 | CFA | +++ | 1.712 @ 1:100 | 0.538 @ 1:100 | +++ | +++ |
| Rabbit 39 | HEXAHIS L1 | Nil | ++ | 0.095 @ 1:100 | 0.050 @ 1:100 | +++ | ? |
| Rabbit 10 | VLPs (baculovirus derived) | Nil | +++ | 0.972 @ 1:100 | 0.487 @ 1:100 | ? | ? |
| Mouse | HEXAHIS L1 | Nil | ++ | ? | ND | ? | ? |
| Mouse | HEXAHIS L1 | CFA | ++++ | 0.400 @ 1:100 | ND | ? | ? |
| MoAb 8 | GST L1 fusion protein | CFA/IFA | ++++ | ++++ | ND | +++ | ? |

LEGENDS

TABLE 2
[a] each group of mice contains four mice
[b] 6b L1 HEXAHIS protein was administered at 50 μg protein per mouse DNA nucleotide sequence and amino acid sequence of HPV6b L1 HEXAHIS protein (SEQ ID NO:5 and 6)
FIG. 2
Electron macrograph of pentameric structures of HPV6b L1 HEXAHIS protein aggregates

We claim:

1. A recombinant papilloma virus L1 protein which has an amino acid sequence shown in FIGS. 1(a)–1(c) (SEQ ID NO:6).

2. A multimeric structure comprising a plurality of recombinant papilloma virus L1 proteins, wherein each of said recombinant papilloma virus L1 proteins is a recombinant papilloma virus L1 protein as claimed in claim 1.

3. A multimeric structure as claimed in claim 2, which is able to induce an immune response that recognizes papilloma virus VLP.

4. A multimeric structure as claimed in claim 2, wherein the multimeric structure is a pentamer.

5. A method for preparing a multimeric structure, comprising:
   (i) expressing in a bacterium a recombinant DNA molecule which encodes a recombinant papilloma virus L1 protein according to claim 1;
   (ii) substantially purifying said recombinant papilloma virus L1 protein; and
   (iii) forming said multimeric structure extracellularly from a plurality of molecules of said papilloma virus L1 protein.

6. A method as claimed in claim 5, wherein the nucleotide sequence encoding said papilloma L1 virus protein is inserted into pTrcHiSB in a correct reading frame with respect to expression of the papilloma virus L1 protein; and wherein said papilloma virus L1 protein is produced by a strain of E. coli.

7. A recombinant papilloma virus L1 protein which has an N terminal amino acid sequence including:
   MetArgGlySerHisHisHisHisHisHisGlyMetAlaSerMetThrGlyGlyGlnMetGlyArgAspLeuTyrAspAspAspAspLysAsp (SEQ ID NO:1).

8. A multimeric structure comprising a plurality of recombinant papilloma virus L1 proteins, wherein each of said recombinant papilloma virus L1 proteins is a recombinant papilloma virus L1 protein as claimed in claim 7.

9. A multimeric structure as claimed in claim 8, which is able to induce an immune response that recognizes papilloma virus VLP.

10. A multimeric structure as claimed in claim 8, wherein the multimeric structure is a pentamer.

11. A method for preparing a multimeric structure, comprising:
   (i) expressing in a bacterium a recombinant DNA molecule which encodes a recombinant papilloma virus L1 protein according to claim 7;
   (ii) substantially purifying said recombinant papilloma virus L1 protein; and
   (iii) forming said multimeric structure extracellularly from a plurality of molecules of said papilloma virus L1 protein.

12. A method as claimed in claim 11, wherein the nucleotide sequence encoding said papilloma virus L1 protein is inserted into pTrcHisB in a correct reading frame with respect to expression of the papilloma virus L1 protein; and wherein said papilloma virus L1 protein is produced by a strain of E. coli.

13. A multimeric structure comprising a plurality of recombinant papilloma virus L1 proteins, wherein each of said recombinant papilloma virus L1 proteins has an N terminal amino acid sequence including $(His)_6$.

14. A multimeric structure as claimed in claim 13 which is able to induce an immune response that recognises papilloma virus VLP.

15. A multimeric structure as claimed in claim 13 wherein the multimeric structure is a pentamer.

16. The multimeric structure of claim 13, wherein said recombinant papilloma virus L1 proteins are bacterially-expressed.

17. A recombinant DNA molecule having a nucleotide sequence selected from any one of the following:
   (a) A nucleotide sequence encoding a recombinant papilloma virus L1 protein and having a 5' nucleotide sequence including:
      ATGCGGGGTTCTCATCATCATCATCAT-CATGGTATGGCTAGCATGACTGGTGGA-CAGCAAATGGGTCGGGATCTGTACGAC-GATGACGATAAGGAT (SEQ ID NO:2);
   (b) A nucleotide sequence that is complementary to the sequence in (a); and
   (c) A nucleotide sequence that is a synonymous sequence to the sequence in (a).

18. A method for preparing a multimeric structure, comprising:
   (i) expressing in a bacterium a recombinant DNA molecule which encodes a recombinant papilloma virus L1 protein comprising an N terminal amino acid sequence including $(His)_6$;
   (ii) substantially purifying said recombinant papilloma virus L1 protein; and
   (iii) forming said multimeric structure extracellularly from a plurality of molecules of said papilloma virus L1 protein,
wherein said recombinant DNA molecule is the recombinant DNA molecule as claimed in claim 17.

19. A method for preparing a multimeric structure, comprising:
   (i) expressing in a bacterium a recombinant DNA molecule which encodes a recombinant papilloma virus L1 protein comprising an N terminal amino acid sequence including:
      MetArgGlySerHisHisHisHisHisHisGlyMetAlaSerMetThrGlyGlyGlnMetGlyArgAspLeuTyrAspAspAspAspLysAsp (SEQ ID NO:1);
   (ii) substantially purifying said recombinant papilloma virus L1 protein; and (iii) forming said multimeric structure extracellularly from a plurality of molecules of said papilloma virus L1 protein wherein said recombinant DNA molecule is the recombinant DNA molecule as claimed in claim 17.

20. A method for preparing a multimeric structure, comprising:

(i) expressing in a bacterium a recombinant DNA molecule which encodes a recombinant papilloma virus L1 protein comprising an amino acid sequence as shown in FIGS. 1(a)–1(c) (SEQ ID NO:6);

(ii) substantially purifying said recombinant papilloma virus L1 protein; and (iii) forming said multimeric structure extracellularly from a plurality of molecules of said papilloma virus L1 protein, wherein said recombinant DNA molecule is the recombinant DNA molecule as claimed in claim 17.

21. A recombinant DNA molecule encoding a recombinant papilloma virus L1 protein and having a 5' nucleotide sequence which includes six repeats of the trinucleotide sequence CAT wherein the recombinant DNA molecule has a nucleotide sequence as shown in FIGS. 1(a)–1(c) (SEQ ID NO:5).

22. A method for preparing a multimeric structure, comprising:

(i) expressing in a bacterium a recombinant DNA molecule which encodes a recombinant papilloma virus L1 protein comprising an N terminal amino acid sequence including $(His)_6$;

(ii) substantially purifying said recombinant papilloma virus L1 protein; and (iii) forming said multimeric structure extracellularly from a plurality of molecules of said papilloma virus L1 protein, wherein said recombinant DNA molecule is the recombinant DNA molecule as claimed in claim 21.

23. A method for preparing a multimeric structure, comprising:

(i) expressing in a bacterium a recombinant DNA molecule which encodes a recombinant papilloma virus L1 protein comprising an N terminal amino acid sequence including:

MetArgGlySerHisHisHisHisHisHisGlyMetAlaSerMetThrGlyGlnMetGlyArgAspLeuTyrAspAspAspAspLysAsp (SEQ ID NO:1);

(ii) substantially purifying said recombinant papilloma virus L1 protein; and (iii) forming said multimeric structure extracellularly from a plurality of molecules of said papilloma virus L1 protein wherein said recombinant DNA molecule is the recombinant DNA molecule as claimed in claim 21.

24. A method for preparing a multimeric structure, comprising:

(i) expressing in a bacterium a recombinant DNA molecule which encodes a recombinant papilloma virus L1 protein comprising an amino acid sequence as shown in FIGS. 1(a)–1(c) (SEQ ID NO:6);

(ii) substantially purifying said recombinant papilloma virus L1 protein; and (iii) forming said multimeric structure extracellularly from a plurality of molecules of said papilloma virus L1 protein, wherein said recombinant DNA molecule is the recombinant DNA molecule as claimed in claim 21.

25. A method for preparing a multimeric structure, comprising:

(i) expressing in a bacterium a recombinant DNA molecule which encodes a recombinant papilloma virus L1 protein which has an N terminal amino acid sequence including $(His)_6$;

(ii) substantially purifying said recombinant papilloma virus L1 protein; and (iii) forming said multimeric structure extracellularly from a plurality of molecules of said papilloma virus L1 protein.

26. The method of claim 25, wherein said DNA molecule comprises a 5' nucleotide sequence having six repeats of the trinucleotide sequence CAT.

27. The method of claim 26, wherein said N terminal amino acid sequence encoding by said DNA comprises:

MetArgGlySerHisHisHisHisHisHisGlyMetAlaSerMetThrGlyGlnMetGlyArgAspLeuTyrAspAspAspAspLysAsp (SEQ ID NO:1).

28. The method of claim 26, wherein said N terminal amino acid sequence encoded by said DNA comprises an amino acid sequence as shown in FIGS. 1(a)–1(c) (SEQ ID NO:6).

29. A method as claimed in claim 25, wherein the nucleotide sequence encoding said papilloma virus L1 protein is inserted into pTrcHisB in a correct reading frame with respect to expression of the papilloma virus L1 protein; and wherein said papilloma virus L1 protein is produced by a strain of *E. coli*.

30. A vaccine, comprising one or more multimeric structures as claimed in any one of claims 13, 14 or 15, together with a pharmaceutically acceptable vaccine adjuvant.

31. A vaccine comprising one or more multimeric structures as claimed in any one of claims 8, 9 or 10, together with a pharmaceutically acceptable vaccine adjuvant.

32. A vaccine comprising one or more multimeric structures as claimed in any one of claims 2, 3 or 4, together with a pharmaceutically acceptable vaccine adjuvant.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 32 amino acids
      (B) TYPE: amino acid
      (C) STRANDEDNESS: single
      (D) TOPOLOGY: linear    (xi) SEQUENCE DESCRIPTION: SEQ ID NO:1:

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30
```

(2) INFORMATION FOR SEQ ID NO:2:

(i) SEQUENCE CHARACTERISTICS:
      (A) LENGTH: 96 base pairs
      (B) TYPE: nucleic acid
      (C) STRANDEDNESS: single
      (D) TOPOLOGY: linear    (xi) SEQUENCE DESCRIPTION: SEQ ID NO:2:

```
ATGCGGGGTT CTCATCATCA TCATCATCAT GGTATGGCTA GCATGACTGG TGGACAGCAA      60

ATGGGTCGGG ATCTGTACGA CGATGACGAT AAGGAT                                96
```

(2) INFORMATION FOR SEQ ID NO:3:

(i) SEQUENCE CHARACTERISTICS:
      (A) LENGTH: 41 base pairs
      (B) TYPE: nucleic acid
      (C) STRANDEDNESS: single
      (D) TOPOLOGY: linear    (xi) SEQUENCE DESCRIPTION: SEQ ID NO:3:

```
GCGGATCCAG ATGTGGCGGC CTAGCGACAG CACAGTATAT G                          41
```

(2) INFORMATION FOR SEQ ID NO:4:

(i) SEQUENCE CHARACTERISTICS:
      (A) LENGTH: 43 base pairs
      (B) TYPE: nucleic acid
      (C) STRANDEDNESS: single
      (D) TOPOLOGY: linear    (xi) SEQUENCE DESCRIPTION: SEQ ID NO:4:

```
CGCCCGGGTT ACCTTTTAGT TTTGGCCTCG CTTACGTTTT AGG                        43
```

(2) INFORMATION FOR SEQ ID NO:5:

(i) SEQUENCE CHARACTERISTICS:
      (A) LENGTH: 1599 base pairs
      (B) TYPE: nucleic acid
      (C) STRANDEDNESS: single
      (D) TOPOLOGY: linear    (ix) FEATURE:
      (A) NAME/KEY: CDS
      (B) LOCATION: 1..1596

(xi) SEQUENCE DESCRIPTION: SEQ ID NO:5:

-continued

| | | | | | | | | | | | | | | | | |
|---|---|---|---|---|---|---|---|---|---|---|---|---|---|---|---|---|
| ATG | CGG | GGT | TCT | CAT | CAT | CAT | CAT | CAT | CAT | GGT | ATG | GCT | AGC | ATG | ACT | 48 |
| Met | Arg | Gly | Ser | His | His | His | His | His | His | Gly | Met | Ala | Ser | Met | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GGT | GGA | CAG | CAA | ATG | GGT | CGG | GAT | CTG | TAC | GAC | GAT | GAC | GAT | AAG | GAT | 96 |
| Gly | Gly | Gln | Gln | Met | Gly | Arg | Asp | Leu | Tyr | Asp | Asp | Asp | Asp | Lys | Asp | |
| | | | 20 | | | | | 25 | | | | | 30 | | | |

| | | | | | | | | | | | | | | | | |
|---|---|---|---|---|---|---|---|---|---|---|---|---|---|---|---|---|
| ATG | TGG | CGG | CCT | AGC | GAC | AGC | ACA | GTA | TAT | GTG | CCT | CCT | CCT | AAC | CCT | 144 |
| Met | Trp | Arg | Pro | Ser | Asp | Ser | Thr | Val | Tyr | Val | Pro | Pro | Pro | Asn | Pro | |
| | | 35 | | | | | 40 | | | | | 45 | | | | |

| | | | | | | | | | | | | | | | | |
|---|---|---|---|---|---|---|---|---|---|---|---|---|---|---|---|---|
| GTA | TCC | AAA | GTT | GTT | GCC | ACG | GAT | GCT | TAT | GTT | ACT | CGC | ACC | AAC | ATA | 192 |
| Val | Ser | Lys | Val | Val | Ala | Thr | Asp | Ala | Tyr | Val | Thr | Arg | Thr | Asn | Ile | |
| | 50 | | | | | 55 | | | | | 60 | | | | | |

| | | | | | | | | | | | | | | | | |
|---|---|---|---|---|---|---|---|---|---|---|---|---|---|---|---|---|
| TTT | TAT | CAT | GCC | AGC | AGT | TCT | AGA | CTT | CTT | GCA | GTG | GGA | CAT | CCT | TAT | 240 |
| Phe | Tyr | His | Ala | Ser | Ser | Ser | Arg | Leu | Leu | Ala | Val | Gly | His | Pro | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| TTT | TCC | ATA | AAA | CGG | GCT | AAC | AAA | ACT | GTT | GTG | CCA | AAG | GTG | TCA | GGA | 288 |
| Phe | Ser | Ile | Lys | Arg | Ala | Asn | Lys | Thr | Val | Val | Pro | Lys | Val | Ser | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| TAT | CAA | TAC | AGG | GTA | TTT | AAG | GTG | GTG | TTA | CCA | GAT | CCT | AAC | AAA | TTT | 336 |
| Tyr | Gln | Tyr | Arg | Val | Phe | Lys | Val | Val | Leu | Pro | Asp | Pro | Asn | Lys | Phe | |
| | | | 100 | | | | | 105 | | | | | 110 | | | |

| | | | | | | | | | | | | | | | | |
|---|---|---|---|---|---|---|---|---|---|---|---|---|---|---|---|---|
| GCA | TTG | CCT | GAC | TCG | TCT | CTT | TTC | GAT | CCC | ACA | ACA | CAA | CGT | TTA | GTA | 384 |
| Ala | Leu | Pro | Asp | Ser | Ser | Leu | Phe | Asp | Pro | Thr | Thr | Gln | Arg | Leu | Val | |
| | | 115 | | | | | 120 | | | | | 125 | | | | |

| | | | | | | | | | | | | | | | | |
|---|---|---|---|---|---|---|---|---|---|---|---|---|---|---|---|---|
| TGG | GCA | TGC | ACA | GGC | CTA | GAG | GTG | GGC | AGG | GGA | CAG | CCA | TTA | GGT | GTG | 432 |
| Trp | Ala | Cys | Thr | Gly | Leu | Glu | Val | Gly | Arg | Gly | Gln | Pro | Leu | Gly | Val | |
| 130 | | | | | 135 | | | | | 140 | | | | | | |

| | | | | | | | | | | | | | | | | |
|---|---|---|---|---|---|---|---|---|---|---|---|---|---|---|---|---|
| GGT | GTA | AGT | GGA | CAT | CCT | TTC | CTA | AAT | AAA | TAT | GAT | GAT | GTT | GAA | AAT | 480 |
| Gly | Val | Ser | Gly | His | Pro | Phe | Leu | Asn | Lys | Tyr | Asp | Asp | Val | Glu | Asn | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| TCA | GGG | AGT | GGT | GGT | AAC | CCT | GGA | CAG | GAT | AAC | AGG | GTT | AAT | GTA | GGT | 528 |
| Ser | Gly | Ser | Gly | Gly | Asn | Pro | Gly | Gln | Asp | Asn | Arg | Val | Asn | Val | Gly | |
| | | | 165 | | | | | 170 | | | | | 175 | | | |

| | | | | | | | | | | | | | | | | |
|---|---|---|---|---|---|---|---|---|---|---|---|---|---|---|---|---|
| ATG | GAT | TAT | AAA | CAA | ACA | CAA | TTA | TGC | ATG | GTT | GGA | TGT | GCC | CCC | CCT | 576 |
| Met | Asp | Tyr | Lys | Gln | Thr | Gln | Leu | Cys | Met | Val | Gly | Cys | Ala | Pro | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| TTG | GGC | GAG | CAT | TGG | GGT | AAA | GGT | AAA | CAG | TGT | ACT | AAT | ACA | CCT | GTA | 624 |
| Leu | Gly | Glu | His | Trp | Gly | Lys | Gly | Lys | Gln | Cys | Thr | Asn | Thr | Pro | Val | |
| | | | 195 | | | | | 200 | | | | | 205 | | | |

| | | | | | | | | | | | | | | | | |
|---|---|---|---|---|---|---|---|---|---|---|---|---|---|---|---|---|
| CAG | GCT | GGT | GAC | TGC | CCG | CCC | TTA | GAA | CTT | ATT | ACC | AGT | GTT | ATA | CAG | 672 |
| Gln | Ala | Gly | Asp | Cys | Pro | Pro | Leu | Glu | Leu | Ile | Thr | Ser | Val | Ile | Gln | |
| 210 | | | | | 215 | | | | | 220 | | | | | | |

| | | | | | | | | | | | | | | | | |
|---|---|---|---|---|---|---|---|---|---|---|---|---|---|---|---|---|
| GAT | GGC | GAT | ATG | GTT | GAC | ACA | GGC | TTT | GGT | GCT | ATG | AAT | TTT | GCT | GAT | 720 |
| Asp | Gly | Asp | Met | Val | Asp | Thr | Gly | Phe | Gly | Ala | Met | Asn | Phe | Ala | Asp | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| TTG | CAG | ACC | AAT | AAA | TCA | GAT | GTT | CCT | ATT | GAC | ATA | TGT | GGC | ACT | ACA | 768 |
| Leu | Gln | Thr | Asn | Lys | Ser | Asp | Val | Pro | Ile | Asp | Ile | Cys | Gly | Thr | Thr | |
| | | | | 245 | | | | | 250 | | | | | 255 | | |

| | | | | | | | | | | | | | | | | |
|---|---|---|---|---|---|---|---|---|---|---|---|---|---|---|---|---|
| TGT | AAA | TAT | CCA | GAT | TAT | TTA | CAA | ATG | GCT | GCA | GAC | CCA | TAT | GGT | GAT | 816 |
| Cys | Lys | Tyr | Pro | Asp | Tyr | Leu | Gln | Met | Ala | Ala | Asp | Pro | Tyr | Gly | Asp | |
| | | | | 260 | | | | | 265 | | | | | 270 | | |

| | | | | | | | | | | | | | | | | |
|---|---|---|---|---|---|---|---|---|---|---|---|---|---|---|---|---|
| AGA | TTA | TTT | TTT | TTT | CTA | CGG | AAG | GAA | CAA | ATG | TTT | GCC | AGA | CAT | TTT | 864 |
| Arg | Leu | Phe | Phe | Phe | Leu | Arg | Lys | Glu | Gln | Met | Phe | Ala | Arg | His | Phe | |
| | | | 275 | | | | | 280 | | | | | 285 | | | |

| | | | | | | | | | | | | | | | | |
|---|---|---|---|---|---|---|---|---|---|---|---|---|---|---|---|---|
| TTT | AAC | AGG | GCT | GGC | GAG | GTG | GGG | GAA | CCT | GTG | CCT | GAT | ACA | CTT | ATA | 912 |
| Phe | Asn | Arg | Ala | Gly | Glu | Val | Gly | Glu | Pro | Val | Pro | Asp | Thr | Leu | Ile | |
| | | 290 | | | | | 295 | | | | | 300 | | | | |

| | | | | | | | | | | | | | | | | |
|---|---|---|---|---|---|---|---|---|---|---|---|---|---|---|---|---|
| ATT | AAG | GGT | AGT | GGA | AAT | CGC | ACG | TCT | GTA | GGG | AGT | AGT | ATA | TAT | GTT | 960 |
| Ile | Lys | Gly | Ser | Gly | Asn | Arg | Thr | Ser | Val | Gly | Ser | Ser | Ile | Tyr | Val | |
| 305 | | | | | 310 | | | | | 315 | | | | | 320 | |

| | | | | | | | | | | | | | | |
|---|---|---|---|---|---|---|---|---|---|---|---|---|---|---|
| AAC | ACC | CCG | AGC | GGC | TCT | TTG | GTG | TCC | TCT | GAG | GCA | CAA | TTG | TTT | AAT | 1008 |
| Asn | Thr | Pro | Ser | Gly | Ser | Leu | Val | Ser | Ser | Glu | Ala | Gln | Leu | Phe | Asn |
| | | | 325 | | | | | 330 | | | | | 335 | | |

```
AAC ACC CCG AGC GGC TCT TTG GTG TCC TCT GAG GCA CAA TTG TTT AAT         1008
Asn Thr Pro Ser Gly Ser Leu Val Ser Ser Glu Ala Gln Leu Phe Asn
            325                 330                 335

AAG CCA TAT TGG CTA CAA AAA GCC CAG GGA CAT AAC AAT GGT ATT TGT         1056
Lys Pro Tyr Trp Leu Gln Lys Ala Gln Gly His Asn Asn Gly Ile Cys
            340                 345                 350

TGG GGT AAT CAA CTG TTT GTT ACT GTG GTA GAT ACC ACA CGC AGT ACC         1104
Trp Gly Asn Gln Leu Phe Val Thr Val Val Asp Thr Thr Arg Ser Thr
            355                 360                 365

AAC ATG ACA TTA TGT GCA TCC GTA ACT ACA TCT TCC ACA TAC ACC AAT         1152
Asn Met Thr Leu Cys Ala Ser Val Thr Thr Ser Ser Thr Tyr Thr Asn
    370                 375                 380

TCT GAT TAT AAA GAG TAC ATG CGT CAT GTG GAA GAG TAT GAT TTA CAA         1200
Ser Asp Tyr Lys Glu Tyr Met Arg His Val Glu Glu Tyr Asp Leu Gln
385                 390                 395                 400

TTT ATT TTT CAA TTA TGT AGC ATT ACA TTG TCT GCT GAA GTA ATG GCC         1248
Phe Ile Phe Gln Leu Cys Ser Ile Thr Leu Ser Ala Glu Val Met Ala
                405                 410                 415

TAT ATT CAC ACA ATG AAT CCC TCT GTT TTG GAA GAC TGG AAC TTT GGG         1296
Tyr Ile His Thr Met Asn Pro Ser Val Leu Glu Asp Trp Asn Phe Gly
            420                 425                 430

TTA TCG CCT CCC CCA AAT GGT ACA TTA GAA GAT ACC TAT AGG TAT GTG         1344
Leu Ser Pro Pro Pro Asn Gly Thr Leu Glu Asp Thr Tyr Arg Tyr Val
        435                 440                 445

CAG TCA CAG GCC ATT ACC TGT CAA AAG CCC ACT CCT GAA AAG GAA AAG         1392
Gln Ser Gln Ala Ile Thr Cys Gln Lys Pro Thr Pro Glu Lys Glu Lys
    450                 455                 460

CCA GAT CCC TAT AAG AAC CTT AGT TTT TGG GAG GTT AAT TTA AAA GAA         1440
Pro Asp Pro Tyr Lys Asn Leu Ser Phe Trp Glu Val Asn Leu Lys Glu
465                 470                 475                 480

AAG TTT TCT AGT GAA TTG GAT CAG TAT CCT TTG GGA CGC AAG TTT TTG         1488
Lys Phe Ser Ser Glu Leu Asp Gln Tyr Pro Leu Gly Arg Lys Phe Leu
                485                 490                 495

TTA CAA AGT GGA TAT AGG GGA CGG TCC TCT ATT CGT ACA GGT GTT AAG         1536
Leu Gln Ser Gly Tyr Arg Gly Arg Ser Ser Ile Arg Thr Gly Val Lys
            500                 505                 510

CGC CCT GCT GTT TCC AAA GCC TCT GCT GCC CCT AAA CGT AAG CGC GCC         1584
Arg Pro Ala Val Ser Lys Ala Ser Ala Ala Pro Lys Arg Lys Arg Ala
        515                 520                 525

AAA ACT AAA AGG TAA                                                      1599
Lys Thr Lys Arg
    530
```

(2) INFORMATION FOR SEQ ID NO:6:

(i) SEQUENCE CHARACTERISTICS:
        (A) LENGTH: 532 amino acids
        (B) TYPE: amino acid
        (D) TOPOLOGY: linear     (ii) MOLECULE TYPE: protein     (xi) SEQUENCE DESCRIPTION: SEQ ID NO:6:

```
Met Arg Gly Ser His His His His His His Gly Met Ala Ser Met Thr
  1               5                  10                  15

Gly Gly Gln Gln Met Gly Arg Asp Leu Tyr Asp Asp Asp Lys Asp
                 20                  25                  30

Met Trp Arg Pro Ser Asp Ser Thr Val Tyr Val Pro Pro Asn Pro
             35                  40                  45

Val Ser Lys Val Val Ala Thr Asp Ala Tyr Val Thr Arg Thr Asn Ile
 50                  55                  60
```

-continued

```
Phe Tyr His Ala Ser Ser Ser Arg Leu Leu Ala Val Gly His Pro Tyr
 65                  70                  75                  80

Phe Ser Ile Lys Arg Ala Asn Lys Thr Val Pro Lys Val Ser Gly
             85                  90                  95

Tyr Gln Tyr Arg Val Phe Lys Val Val Leu Pro Asp Pro Asn Lys Phe
            100                 105                 110

Ala Leu Pro Asp Ser Ser Leu Phe Asp Pro Thr Thr Gln Arg Leu Val
            115                 120                 125

Trp Ala Cys Thr Gly Leu Glu Val Gly Arg Gly Gln Pro Leu Gly Val
            130                 135                 140

Gly Val Ser Gly His Pro Phe Leu Asn Lys Tyr Asp Asp Val Glu Asn
145                 150                 155                 160

Ser Gly Ser Gly Gly Asn Pro Gly Gln Asp Asn Arg Val Asn Val Gly
                165                 170                 175

Met Asp Tyr Lys Gln Thr Gln Leu Cys Met Val Gly Cys Ala Pro Pro
            180                 185                 190

Leu Gly Glu His Trp Gly Lys Gly Lys Gln Cys Thr Asn Thr Pro Val
            195                 200                 205

Gln Ala Gly Asp Cys Pro Pro Leu Glu Leu Ile Thr Ser Val Ile Gln
            210                 215                 220

Asp Gly Asp Met Val Asp Thr Gly Phe Gly Ala Met Asn Phe Ala Asp
225                 230                 235                 240

Leu Gln Thr Asn Lys Ser Asp Val Pro Ile Asp Ile Cys Gly Thr Thr
            245                 250                 255

Cys Lys Tyr Pro Asp Tyr Leu Gln Met Ala Ala Asp Pro Tyr Gly Asp
            260                 265                 270

Arg Leu Phe Phe Phe Leu Arg Lys Glu Gln Met Phe Ala Arg His Phe
            275                 280                 285

Phe Asn Arg Ala Gly Glu Val Gly Glu Pro Val Pro Asp Thr Leu Ile
290                 295                 300

Ile Lys Gly Ser Gly Asn Arg Thr Ser Val Gly Ser Ser Ile Tyr Val
305                 310                 315                 320

Asn Thr Pro Ser Gly Ser Leu Val Ser Ser Glu Ala Gln Leu Phe Asn
                325                 330                 335

Lys Pro Tyr Trp Leu Gln Lys Ala Gln Gly His Asn Asn Gly Ile Cys
            340                 345                 350

Trp Gly Asn Gln Leu Phe Val Thr Val Val Asp Thr Thr Arg Ser Thr
            355                 360                 365

Asn Met Thr Leu Cys Ala Ser Val Thr Thr Ser Ser Thr Tyr Thr Asn
370                 375                 380

Ser Asp Tyr Lys Glu Tyr Met Arg His Val Glu Glu Tyr Asp Leu Gln
385                 390                 395                 400

Phe Ile Phe Gln Leu Cys Ser Ile Thr Leu Ser Ala Glu Val Met Ala
            405                 410                 415

Tyr Ile His Thr Met Asn Pro Ser Val Leu Glu Asp Trp Asn Phe Gly
            420                 425                 430

Leu Ser Pro Pro Pro Asn Gly Thr Leu Glu Asp Thr Tyr Arg Tyr Val
            435                 440                 445

Gln Ser Gln Ala Ile Thr Cys Gln Lys Pro Thr Pro Glu Lys Glu Lys
            450                 455                 460

Pro Asp Pro Tyr Lys Asn Leu Ser Phe Trp Glu Val Asn Leu Lys Glu
465                 470                 475                 480

Lys Phe Ser Ser Glu Leu Asp Gln Tyr Pro Leu Gly Arg Lys Phe Leu
            485                 490                 495
```

-continued

```
Leu Gln Ser Gly Tyr Arg Gly Arg Ser Ser Ile Arg Thr Gly Val Lys
            500                 505                 510

Arg Pro Ala Val Ser Lys Ala Ser Ala Ala Pro Lys Arg Lys Arg Ala
            515                 520                 525

Lys Thr Lys Arg
        530
```